(12) United States Patent
Nakamura et al.

(10) Patent No.: US 10,058,590 B2
(45) Date of Patent: Aug. 28, 2018

(54) METHODS OF TREATING AMYOTROPHIC LATERAL SCLEROSIS BY HGF

(71) Applicant: Toshikazu Nakamura, Kyoto-shi, Kyoto (JP)

(72) Inventors: Toshikazu Nakamura, Osaka (JP); Hiroshi Funakoshi, Osaka (JP); Woong Sun, Seoul (KR)

(73) Assignee: TOSHIKAZU NAKAMURA, Kyoto (JP)

( * ) Notice: Subject to any disclaimer, the term of this patent is extended or adjusted under 35 U.S.C. 154(b) by 0 days.

(21) Appl. No.: 15/399,211

(22) Filed: Jan. 5, 2017

(65) Prior Publication Data

US 2017/0112902 A1     Apr. 27, 2017

Related U.S. Application Data

(63) Continuation of application No. 10/380,522, filed as application No. PCT/JP01/01539 on Feb. 28, 2001.

(30) Foreign Application Priority Data

Sep. 14, 2000   (JP) ................ 2000-280081

(51) Int. Cl.
| | | |
|---|---|---|
| *A61K 38/00* | (2006.01) | |
| *A61K 38/18* | (2006.01) | |
| *A61K 49/00* | (2006.01) | |
| *C07K 14/475* | (2006.01) | |
| *C07K 14/48* | (2006.01) | |
| *C07K 14/00* | (2006.01) | |
| *A61K 48/00* | (2006.01) | |

(52) U.S. Cl.
CPC .......... *A61K 38/1833* (2013.01); *A61K 48/00* (2013.01)

(58) Field of Classification Search
CPC ........ A61K 2300/00; A61K 2267/0356; A61K 33/00; A61K 38/00; A61K 38/185; A61K 9/0085; C12N 5/0619; C12N 15/85; G01N 2500/10; G01N 33/5058; A01K 2267/0318; A01K 2267/0356
See application file for complete search history.

(56) References Cited

U.S. PATENT DOCUMENTS 6,143,714 A    11/2000  Wong et al.

FOREIGN PATENT DOCUMENTS

| EP | 0722737 A1 | 7/1996 |
| EP | 0846764 A2 | 6/1998 |
| JP | 10337189 A | 12/1998 |
| WO | 9739629 A1 | 10/1997 |

OTHER PUBLICATIONS

Beckman, "Nerve Verve", Science of Aging Knowledge Environment, Aug. 14, 2002.
Cheah et al., "Riluzole, Neuroprotection and Amyotrophic Lateral Sclerosis", Current Medicinal Chemistry, (2010), vol. 17, pp. 1942-1959.
Goyal et al., "Experimental trials in amyotrophic lateral sclerosis: a review of recently completed, ongoing and planned trials using existing and novel drugs", Expert Opinion Investig. Drugs, (2014) vol. 23 No. 11 pp. 1541-1551.
Henriques et al., "Neurotrophic growth factors for the treatment of amyotrophic lateral sclerosis: where do we stand?" Frontiers in Neuroscience, Jun. 2010, vol. 4, No. 32 pp. 1-14.
Okano, "The First Clinical Trial in Tohoku University Hospital after the Great East Japan Earthquake: The Heroic Efforts of My Friend, Professor Masashi Aoki", The Keio Journal of Medicine (2012), vol. 61. No. 1, pp. 3-9.
Guillot et al., "Local GDNF expression mediated by lentiviral vector protects facial nerve motoneurons but not spinal motoneurons in SOD1 G93A transgenic mice", Neurobiology of Disease, (2004) vol. 16. pp. 139-149.
Barshes et al., "Anatomy and Physiology of the Leptomeninges and CSF Space", Cancer Treat. Res. (2002) Cole 125, pp. 1-16.
"The ALS Newsletter" MDA Publications, (2001), vol. 6 No. 1, pp. 1-8.
Sakka et al., "Anatomy and physiology of cerebrospinal fluid", European Annals of Otorhinolaryngology, Head and Neck disease, (2011) vol. 128, pp. 309-316.
Yaksh et al., "Kinetic and Safety Studies on Intrathecally Infused Recombinant-Methionyl Human Brain-Derived Neurotrophic Factor in Dogs", Fundamental and Applied Toxicology, vol. 38, pp. 89-100 (1997).
Ishigaki et al., "Intrathecal Delivery of Hepatocyte Growth Factor From Amyotriphic Lateral Sclerosis Onset Suppresses Disease Progression in Rat Amyotrophic Lateral Sclerosis Model", J. Neuropathol Exp Neurol, vol. 66, No. 1, pp. 1037-1044 Nov. 2007.
Hiroshi Mitsumoto; Neurotrophic factors as the therapeutic agents for ALS; Advances in Neurological Sciences; vol. 44; No. 3; pp. 482-490; 2000.
Lin, C. L. Glenn, et al., "Aberrant RNA Processing in a Neurodegenerative Disease: the Cause for Absent EAAT2, a Glutamate Transporter, in Amyotrophic Lateral Sclerosis," Neuron, vol. 20, pp. 589-602 (1998).
Aebischer, P., et al., "Intrathecal delivery of CNTF using encapsulated genetically modified xenogeneic cells in amyotrophic lateral sclerosis patients," Nature Medicine, vol. 2, pp. 696-699.
Funokoshi, H., et al., Program of the 23rd Annual Meeting of the Japan Neuroscience Society, vol. 23, pp. 245-551, Sep. 4, 2000.

(Continued)

*Primary Examiner* — Chang-Yu Wang
(74) *Attorney, Agent, or Firm* — Roberts Mlotkowski Safran Cole & Calderon, P.C.

(57) ABSTRACT

The invention presents a therapeutic agent (and progress suppressant) for amyotrophic lateral sclerosis (ALS) containing HGF and/or HGF gene as active ingredient. HGF has an effect of improving the motor function of ALS and life span through two actions, that is, direct neuronutrient factor activity on motoneurons, and indirect improving action of glutamate cytotoxicity on motoneurons by maintaining the level of glutamate transporter in astrocytes. Hence, HGF and/or HGF gene can be used as an effective therapeutic agent not known in the past.

11 Claims, 12 Drawing Sheets

(56) References Cited

OTHER PUBLICATIONS

Okura et al. Eur. J. Neurosci. 1999. 11:4139-4144.
Mandel et al. Curr Opin Mol Ther. Oct. 2004;6(5):482-90.
Wong et al. Hum. Gene Thera. 2006. 17: 1-9.
Ryan et al. Expert Opin. Biol Ther 2007. 7:305-18.
Jarvelainen et al. Trends in Cell Biology. 2003. 13:204-209.
Sanchez Mejia et al., The Neuroscientist. 2001. 7: 480-9.
Sen et al. Mol. Cell. Biochem. 2003.253:241-246.
Proper et al., Brain. 2002. 125:32-43.
Cimarosti et al. Neurosci. Lett. 2005. 385: 52-57.
Ohnuma et al., Prog. Neuro-Psychopharm. Biol. Psych. 2005. 29: 889-894.
M. Li et al., Science, vol. 288, pp. 335-339, Apr. 14, 2000.
M. Figiel et al., Experimental Neurology, vol. 183, pp. 124-135, 2003.
H. Guo et al., Human Molecular Genetics, vol. 12, No. 19, pp. 2519-2532, 2003.
L. I. Bruijn et al., Neuron, vol. 18, pp. 327-338, Feb. 1997.
J. D. Rothstein et al., Annals of Neurology, vol. 38, No. 1, pp. 73-84, Jul. 1995.
Bruijn et al. Annu. Rev. Neurosci. 2004, 27: 723-49.
Rothstein Curr. Opin. In Neurobiol. 1996. 6: 679-687.
Gurney et al., Science, vol. 264, pp. 1772-1775 (Jun. 17, 1994).
Nakamura et al., Biochemical and Biophysical Research Communications, vol. 122, No. 3, pp. 1450-1459 (Aug. 16, 1984).
Nakamura et al., Nature, vol. 342, pp. 440-443 (Nov. 23, 1989).
Matsumoto and Nakamura, pp. 198-211 in "Plasminogen-Related Growth Factors", (Ciba Foundation Symposium 212). c. 1957 by Wiley, Chichester.
Maina et al., Nature Neuroscience, vol. 2, No. 3, pp. 213-217 (Mar. 1999).
Honda et al., Molecular Brain Research, vol. 32, pp. 197-210 (1995).
Ebens et al. Neuron, vol. 17, pp. 1157-1172 (Dec. 1996).
Novak et al., The Journal of Neuroscience, vol. 20, No. 1, pp. 326-337 (Jan. 1, 2000).
Funakoshi et al., Advances in Neurological Sciences, vol. 41, No. 6, pp. 885-898 (1997).
Annual Report of the Group Research in the Pathogenesis and Pathomechanism of Amytropic Lateral Sclerosis (1999).
Funakoshi, Hiroshi et al., Kin Ishukusei Sokusaku Koukashou No Seiin to Byoutai Ni Kansuru Kenkyuuhan, Heisei 11 Nendo, Kenkyuu Houkokusho, pp. 11-13, Mar. 2000.
Hiruma, Hiromi et al., Kin Ishukusei Sokusaku Koukashou No Seiin to Byoutai Ni Kansuru Kenkyuuhan, Heisei 11 Nendo, Kenkyuu Houkokusho, p. 28, Mar. 2000.
Katsuta, Hitoshi. Kin Ishukusei Sokusaku Koukashou No Seiin to Byoutai Ni Kansuru Kenkyuuhan, Heisei 11 Nendo, Kenkyuu Houkokusho, p. 35, Mar. 2000.
Aoki, Masashi. Brain Medical, vol. 12, No. 2, pp. 72-76, Jun. 2000.
Sun, W., et al., Society for Neuroscience Abstracts, 26(1-2), Abstract No. 27.6.2300.
Yamamoto, M., et al. Society for Neuroscience Abstracts, 26(1-2), Abstract No. 507.6.2000.

METHODS OF TREATING AMYOTROPHIC LATERAL SCLEROSIS BY HGF

This application is a Continuation Application of U.S. application Ser. No. 10/380,522, filed Mar. 14, 2003 and now abandoned, which in turn is the National Stage application of PCT/JP01/01539, which has an international filing date of Feb. 28, 2001, and which designated the United States of America. This application also claims priority under 35 USC § 119(a)-(d) of JP application 2000-280081, filed Sep. 14, 2000, in Japan. All of these prior applications are hereby incorporated by reference in their entirety and for all purposes.

TECHNICAL FIELD

The present invention relates to a remedy for amyotrophic lateral sclerosis (ALS). More particular, the invention relates to a remedy for ALS containing HGF (hepatocyte growth factor) and/or HGF genes as active ingredients.

BACKGROUND ART

Amyotrophic lateral sclerosis (ALS) is a severe neurodegenerative disease characterized by progressive loss of motoneurons and degeneration of motor axons, which results in motor dysfunction and shortening of life span. About 15% of ALS patients are patients with familial ALS (FALS), and about 15% to 25% of FALS patients carry mutations in the gene encoding $Cu^{2+}/Zn^{2+}$ superoxide dismutase (SOD1). Transgenic mice with high levels of mutant SOD1 protein and activity develop diseases similar to both familial and sporadic ALS, and such muted SOD1 overexpressing transgenic mice are used as a model for ALS. In the invention, too, G93A mice (Science, 264, 1772-1775, 1994) were used as muted SOD1 (G93A) overexpressing transgenic mice.

Since degeneration of motoneurons is thought to be a first sign of the disease, many approaches had been focused to directly support the survival of motoneurons. However, these attempts were not satisfactory.

On the other hand, Brujin et al. reported that prominent SOD1 containing inclusions in astrocytes appear prior to clinical signs and increase markedly in abundance during disease progression, implicating astrocytes as primary targets for mutant-SOD1 mediated damage in mutant SOD1 (G85R) overexpressing transgenic mice (Neuron, 18, 327-338, 1997). Therefore, a bifunctional substance that can restore the function of astrocytes and directly promote motoneurons from each cell death would be more ideal for the treatment of ALS. Such substance, however, has not been known yet.

Hepatocyte growth factor (HGF) was first identified as a potent mitogen for mature hepatocytes, and its gene was cloned in 1989 (Biochem. Biophys. Res. Commun., 122, 1450-1459, 1984; Nature, 342, 440-443, 1989). Although HGF was discovered as a hepatotrophic factor, recent extensive studies on expression and functional analysis including knockout/in mice strategies revealed HGF as a new neurotrophic factor (Ciba. Found. Symp., 212, 198-211, 1997; Nat. Neurosci., 2, 213-217, 1999). HGF shows neurotrophic activities on hippocampus, cerebral cortex, midbrain dopaminergic, cerebellum granular, sensory and motoneurons and sympathetic neuroblasts (Ciba. Found. Symp., 212, 198-211, 1997; Brain Res. Mol. Brain Res., 32, 197-210, 1995). Especially, HGF is shown to be one of the most potent survival promoting factors for motoneurons comparable with glial cell line derived neurotrophic factors (GDNF) in vitro (Neuron, 17, 1157-1172, 1996). Neurotrophic effects of HGF on embryonic spinal motor neurons during development and on adult motor neurons after axotomy of hypoglossal nerve are shown in vivo (J. Neurosci., 20, 326-337, 2000; Eur. J. Neurosci., 11, 4139-4144, 1999). However, nothing has been reported about the role of HGF in ALS, or clinical effect of expression of HGF on ALS, and therefore it has been known whether HGF would be a remedy for ALS or not.

In this background, the present inventors investigated into possibility of using HGF as a remedy for ALS in order to present a novel remedy for ALS.

The inventors first studied the role of HGF in ALS by using G93A transgenic mice as a model for ALS. As a result, it is found that c-Met/HGF receptor-like immunoreactivity (c-Met-IR) is localized in motoneurons of G93A transgenic mice similarly to that of wildtype littermates. Quantification of the levels of the expression of c-met and HGF mRNA in the ventral horn of spinal cord (where motoneurons locate) revealed that they were progressively increased during the progression of ALS in G93A transgenic mice. These results suggested the roles of HGF on ALS motoneurons.

Using neuron-specific enolase promoter (NSE), the inventors generated transgenic mice overexpressing rat HGF in a neuron-specific manner, and explored the effect of HGF on ALS. As a result, it was discovered for the first time that HGF is effective to attenuate motoneuronal death and suppress axonal degeneration of motoneurons. It was also found that HGF exerts a neuroprotective effect not only on motoneurons but also on DRG sensory neurons against ALS related neurotoxicity. The neuroprotective effect of HGF was also indicated from the delayed loss of muscle weight in ALS.

The inventors further studied if the progress of ALS can be actually suppressed (delayed) by HGF or not by using the same transgenic mice. To a great surprise, start of paralysis was delayed, the life span was extended, and motor functions were improved by an extremely small expression of HGF (about 2 times of wildtype mouse and G93A mouse).

On the basis of these findings, it was discovered for the first time that the HGF has a therapeutic effect on ALS.

The inventors further investigated into the mechanism of suppressing progress of ALS by HGF, and revealed that HGF brings about the ALS improving effects by at least three new mechanisms as explained below.

(1) Induction Suppressing Action of Caspase-1 on Motoneurons

At middle stage of ALS, caspase-1 is thought to play an important role in the progress of the disease, because caspase-1 is shown to be activated and/or induced in motoneurons of transgenic mice overexpressing mutated SOD1 (Proc. Natl. Acad. Sci. U.S.A., 95, 15763-15768, 1998; Science, 288, 335-339, 2000), and introduction of dominant negative inhibitor for caspase-1 in G93A mice was successfully delayed in mortality for about 2 weeks (Nature, 388, 31, 1997; J. Exp. Med., 185, 933-940, 1997). Accordingly, the inventors examined whether HGF can modify the induction of caspase-1, and disclosed that HGF has an effect of suppressing induction of caspase-1 in ALS motoneurons.

(2) Phosphorylation of Akt in Spinal Cord

Phosphorylation of Akt is suggested to be involved in the survival promoting activity of HGF in cerebral cortex neurons and kidney epithelial cells, and HGF is shown to induce Bcl-xl expression and block massive apoptosis in the liver in fluminant hepatitis models (Biochem. Biophys. Res. Commun., 244, 683-690, 1998; Hepatology, 30, 151-159, 1999).

Accordingly, the present inventors explored if phosphorylation of Akt would be induced by expression of HGF, and recognized phosphorylation of Akt specifically in the spinal cord of ALS.

(3) Suppression of Down-regulation of Glial-specific Glutamate Transporter (EAAT2/GLT1) in Reactive Astrocytes It has been indicated that glutamate-mediated excitotoxicity contributes to motor neuron degeneration of ALS by reduction of glutamate clearance.

Consistently with this hypothesis, it is reported that in the spinal cord and motor cortex of patients with sporadic ALS, glutamate transport activity is decreased remarkably (N. Engl. J. Med., 326, 1464-1468, 1992), and immunoreactivity for glial-specific glutamate transporter (EAAT2/GLT-1), which locates in astrocytes and is thought to be a major transporter to suppress glutamatergic neurotoxicity, selectively disappears (Ann. Neurol., 38, 73-84, 1995). The reduction of EAAT2 in G85R type ALS model transgenic mice (Neuron, 18, 327-338, 1997), and SOD1 mutants (A4V and I113T)-linked inactivation of a glial glutamate transporter in ALS (Nat. Neurosci., 2, 427-433, 1999) are also reported. The inventors previously studied the role of HGF on EAAT2 because glutamatergic neurotoxicity was thought to play a part in motoneuron degeneration in ALS. As a result, it was found that HGF functions to suppress down-regulation of EAAT2 in ALS and maintain a functional astrocytes in endstage of ALS.

It was thus disclosed that HGF improves ALS by at least three mechanisms, that is, induction suppressing action of caspase –1 on motoneurons, phosphorylation of Akt, and suppression of down-regulation of glial-specific glutamate transporter (EAAT2/GLT1) in reactive astrocytes.

Thus, HGF has an effect of improving the motor function of ALS and life span through two actions, that is, direct neuronutrient factor activity on motoneurons, and indirect improving action of glutamate cytotoxicity on motoneurons by maintaining the level of glutamate transporter in astrocytes. Such bifunctional growth factor has not bee known so far, and HGF is a first example. Such functions of HGF suggest possibility therapeutic usefulness of HGF (gene or protein) in ALS and related motoneuron diseases.

SUMMARY OF THE INVENTION

The invention is devised on the basis of the above findings. That is, the invention presents:

(1) Remedy for ALS, containing HGF and/or HGF gene as active ingredient.

(2) Progress suppressant for ALS, containing HGF and/or HGF gene as active ingredient.

(3) Induction suppressant of caspase-1 in motoneurons, containing HGF and/or HGF gene as active ingredient.

(4) Phosphorylation promoter of Akt in spinal cord, containing HGF and/or HGF gene as active ingredient.

(5) Decrease suppressant of glial-specific glutamate transporter (EAAT2/GLT-1) in astrocytes, containing HGF and/or HGF gene as active ingredient.

DETAILED DESCRIPTION OF PREFERRED EMBODIMENT

Figure 1:
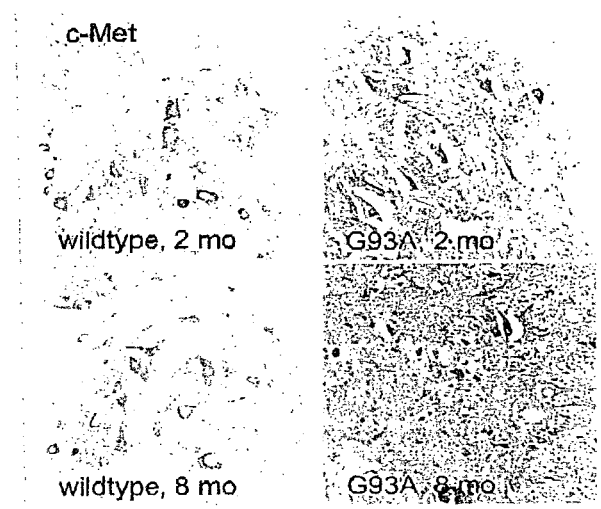
FIG. 1 is a microphotograph showing results of immunohistological analysis of expression of c-Met (C-Met-IR) in motoneurons in G93A transgenic mice (G93A) and wildtype littermates (wildtype). In the figure, 2 mo denotes 2 months of age, and 8 mo is 8 months of age.

HGF used in the invention is a known substance, and its base sequence and amino acid sequence are disclosed, for example, in Nature, 342, 440 (1989), Japanese Patent No. 2777678, Biochem. Biophys. Res. Commun., 163, 967 (1989), Biochem. Biophys. Res. Commun., 172, 321 (1990), etc. This HGF may be manufactured in any method as far as it is refined to be a pharmaceutical level. Commercial products may be also used (for example, Code No. HGF-101 of Toyobo).

For example, HGF may be manufactured by cultivating primary culture cells or established cells producing HGF, and obtaining HGF by separating and purifying from the culture supernatant. Or, by a gene engineering technique, a gene encoding HGF is incorporated in a proper vector, and it is inserted into a proper host to transform, and a desired recombinant HGF can be obtained from the culture supernatant of this transformant (for example, see Nature, 342, 440, 1989; Japanese Laid-open Patent No. 5-111383, Biochem. Biophys. Res. Commun., 163, 967, 1989, etc.). The host cell is not particularly limited, and various host cells hitherto used in the gene engineering techniques can be used, such as *Escherichia coli*, yeast or animal cells. Animal cells include CHIO cell, COS cell, and mouse C127 cell (all available from ATCC, etc.). Thus obtained HGF may have a structure analogous to natural type HGF as far as it has an action substantially same as natural type HGF. That is, the category of HGF of the invention includes protein having action as HGF among 1) protein encoded by DNA for hybridizing with cDNA of HGF in stringent conditions, and 2) protein of amino acid sequence having one or plural (preferably several) amino acids replaced, deleted and/or added in the amino acid sequence of HGF. Herein, the DNA for encoding the protein of 1) or 2) can be obtained easily, for example, by site-specific mutagenesis induction method, PCR method, or ordinary hybridization method, and specifically it can be executed by reference to the textbook "Molecular Cloning 2nd Ed.," Cold Spring Harbor Laboratory Press (1989), or the like.

The invention has disclosed for the first time that HGF is useful as remedy for ALS, specifically as progress suppressant of ALS. HGF has an effect of improving the motor function of ALS and life span through two actions, that is, direct neuronutrient factor activity on motoneurons, and indirect improving action of glutamate cytotoxicity on motoneurons by maintaining the level of glutamate transporter in astrocytes. Such bifunctional growth factor has not been known in the past, and HGF is a first example. Having these two actions, HGF is capable of retarding and suppressing the progress of ALS and related motoneuron diseases.

As the mechanism of action of HGF on ALS, HGF is considered to have ALS improving effects by exhibiting at least the following three actions.

(1) Induction suppressing action of caspase −1 on motoneurons (2) Phosphorylation of Akt in spinal cord (3) Suppression of down-regulation of glial-specific glutamate transporter (EAAT2/GLT1) in reactive astrocytes Endogenous growth factor having such action has not been known hitherto, and HGF is a first growth factor showing these actions. By exhibiting these actions, HGF can retard or suppress the progress of ALS and related motoneuron diseases.

Motoneuron diseases relating to ALS include progressive spinal muscular atrophy, progressive bulbar paralysis, primary lateral sclerosis, infantile or juvenile muscular atrophy, Fazio-Londe syndrome, Charcot-Marie-Tooth disease, and others, but are not limited to these diseases.

The remedy of the invention may be prepared in various pharmaceutical formulas (such as liquid and solid), but generally it is manufactured as an injection of active ingredient of HGF only or together with a usual carrier. The injection can be prepared in an ordinary method, and, for example, HGF is dissolved in a proper solvent (for example, sterilized water, buffer solution, physiological saline), and filtered and sterilized by a filter, and poured into an aseptic container. The content of HGF in the injection is usually adjusted to be 0.0002 to 0.2 w/v %, preferably about 0.001 to 0.2 w/v %.

In pharmaceutical manufacture, preferably, a stabilizer is added, and examples of the stabilizer include albumin, globulin, gelatin, mannitol, glucose, dextran, and ethylene glycol. Further, the preparation of the invention may include additives necessary for manufacture, such as vehicle, dissolution aid, antioxidant, analgesic, and isotonic agent. In a form of liquid preparation, it is preferable to store it under frozen conditions or after the removal of water by a process such as freeze-drying. The freeze-dry preparation is used by adding distilled water for injection and redissolving.

The preparation of the invention is administered through a proper route depending on the dosage form. The route of administration is not particularly limited as far as HGF acts properly to suppress progress of ALS. General routes are subcutaneous administration, intradermal administration, intravenous administration, intra-aortic administration, muscular administration, local injection, intraventricular administration, and intraspinal administration. Further, it may be administered through a device embedded in the body, and specifically it may be administered to the diseased site continuously and gradually by using a osmotic pump or the like, or a sustained-release agent (for example, mini pellet preparation) may be buried near the diseased site.

In particular, the intraspinal administration is a preferred route because the preparation of the invention can reach the motoneurons in the spinal cord directly.

The dose is adjusted properly depending on the symptom, age, body weight and other conditions of patients, and usually the dose of HGF is 0.001 mg to 1000 mg, preferably 0.01 mg to 100 mg, which is divided in one to several portions a day.

As described in Examples below, it was proved that ALS was improved by expression of a very small amount of HGF. That is, by the HGF expression level of about 2 times of the HGF expression amount in the spinal cord of wildtype mice and G93A transgenic mice, the motor function was improved sufficiently at 6 months in the period of first sign of symptoms of ALS, and the life was expanded by 1 month in mice. Therefore, for patients with ALS, the HGF preparation of the invention is preferred to be administered at a dose of more than 2 times before HGF administration at least in the HGF expression level in the spinal cord. The invention also presents a remedy for ALS at a dose of more than 2 times before HGF administration, as the HGF expression level in the spinal cord.

Recently, gene therapies using HGF gene have been reported (see Circulation, 96, No. 3459, 1997; Nature Medicine, 5, 226-230, 1999; Circulation, 100, No. 1672, 1999; Gene Therapy, 7, 417-427, 2000, etc.), and this method is established technically. The invention includes not only the administration of HGF protein as mentioned above, but also a gene remedy for ALS by transducing HGF. The gene therapy of HGF is explained below.

The HGF gene used in the invention refers to the gene capable of expressing HGF (HGF protein). More specifically, cDNA of HGF mentioned in Nature, 342, 440 (1989), Japanese Patent No. 2777678, Biochem. Biophys. Res. Commun., 163, 967 (1989), Biochem. Biophys. Res. Commun., 172, 321 (1990), etc. is incorporated in a proper expressing vector (non-viral vector, viral vector). The base sequence of the cDNA encoding HGF is mentioned in the above documents, and is also registered in the database of Genbank and others. On the basis of such sequence information, a proper DNA portion is used as primary of PCR, and, for example, by RT-PCR reaction on the m-RNA derived from liver or leukocytes, cDNA of HGF can be cloned. Such cloning operations can be done easily by those skilled in the art by referring to the textbook such as "Molecular Cloning 2nd Ed.," Cold Spring Harbor Laboratory Press (1989).

Further, the HGF gene of the invention is not limited to those mentioned above, and as far as the expressed protein substantially as the same action as HGF, it can be used as the HGF gene of the invention. That is, among 1) DNA for hybridizing in stringent conditions with the above-mentioned cDNA, and 2) DNA for encoding protein of amino acid sequence having one or plural (preferably several) amino acids replaced, deleted and/or added in the amino acid sequence of the protein encoded by the cDNA, those capable of protein having the action as HGF are included in the category of the HGF gene of the invention. Herein, the DNA of 1) or 2) can be obtained easily, for example, by site-specific mutagenesis induction method, PCR method, or ordinary hybridization method, and specifically it can be executed by reference to the textbook such as "Molecular Cloning" mentioned above.

The HGF gene of the invention can be applied in the same diseases as the HGF protein. The HGF gene and HGF protein can be used independently or in combination.

The gene transducing method, transducing format and transducing amount used in the gene therapy of the invention are described below.

When the gene remedy mainly composed of gene as active ingredient is administered to patients, modes of administration are roughly classified into a method of using non-viral vector and a method of using viral vector, and the preparation and administration are specifically described in the textbooks (Supplementary Experimental Medicine, Fundamental technology of gene therapy, Yodosha, 1996; Supplementary Experimental Medicine, Gene transduction and expression analysis experiment, Yodosha, 1997; Gene therapy development research handbook edited by Japan Society of Gene Therapy, N T S, 1999). These methods are specifically described below.

A. Using Non-viral Vector

Using a recombination expression vector having an intended gene integrated in a usual gene expression vector, the intended gene can be transduced into the cell or tissue in the following technique.

The gene transducing method into a cell includes lipofection method, phosphoric acid-calcium coprecipitation method, DEAE-dextran method, and DNA direct injection method using micro glass tube.

The gene transducing method into a tissue includes gene transduction method by internal type liposome, gene transduction method by electrostatic type liposome, HVJ-liposome method, modified HVJ-liposome method (HVJ-AVE liposome method), receptor interstitial gene transduction method, method of transcribing DNA molecule into cell together with carrier (metal particle) by particle gun, naked-DNA direct transduction method, and method of transduction by positive charge polymer, and a recombination expression vector can be integrated into the cell.

In particular, the HVJ-liposome is prepared by sealing DNA into liposome composed of lipid double membrane, and fusing this liposome and inactivated hemagglutinating virus of Japan (HVJ). As compared with the conventional liposome method, the HVJ-liposome method is very high in the fusion activity with cell membrane, and it is a preferred form of transduction. The preparing method of HVJ-liposome is taught in the publications (Supplementary Experimental Medicine, Fundamental technology of gene therapy, Yodosha, 1996; Supplementary Experimental Medicine, Gene transduction and expression analysis experiment, Yodosha, 1997; J. Clin. Invest. 93, 1458-1464, 1994; Am. J. Physiol. 271, R1212-1220, 1996), which should be referred to. Preferably, HVJ should be obtained from Z strain (available via ATCC), but basically other HVJ strains (for example, ATCC VR-907 or ATCC VR-105) may be also used.

The direct transduction method of naked-DNA is the easiest method of all methods mentioned above, and is hence a preferred method of transduction.

The expression vector used herein may be any expression vector as far as the intended gene can be expressed in the body, and recommended expression vectors include pCAGGS (Gene 108, 193-200, 1991), pBK-CMV, pcDNA3.1, pZeoSV (Invidrogen Co., Stratagene Co.).

B. Using Viral Vector

As the viral vector, recombinant adeno virus, retro virus, and other viral vectors are used. More specifically, by using detoxicated retro virus, adeno virus, adeno companion virus, herpes virus, vaccinia virus, pox virus, polio virus, Sindbis virus, hemagglutinating virus of Japan, SV40, human immunodeficiency virus (HIV), other DNA virus, or RNA virus, an intended gene is transduced, and the cell is infected with the recombinant virus, and the gene can be transduced into the cell.

Of these viral vectors, the infection efficiency of adeno virus is known to be very high as compared with other viral vectors, and from this viewpoint it is preferred to use the adeno virus vector system.

The method of administration of the gene remedy of the invention into patients includes both in-vivo method of introducing the gene remedy directly into the body, and ex-vivo method of taking out a certain cell from the body, transducing the gene remedy into the cell, and putting back the cell into the body (Nikkei Science, 20-45, April 1994; Monthly Pharmacology, 36 (1), 23-48, 1994; Experimental Medicine Extra, 12 (15), 1994; Gene Remedy Development Research Handbook ed. by Japan Society of Gene Therapy, N T S, 1999). In this invention, the in-vivo method is preferred.

The route of administration to patient is not particularly specified as far as HGF expressed in the body can exhibit its action to suppress progression of ALS. General routes are subcutaneous administration, intradermal administration, intravenous administration, intra-aortic administration, muscular administration, local injection, intraventricular administration, and intraspinal administration. Further, it may be administered through a device embedded in the body, and specifically it may be administered to the diseased site continuously and gradually by using a osmotic pump or the like, or a sustained-release agent (for example, mini pellet preparation) may be buried near the diseased site.

Above all, the intraspinal administration is a preferred route of administration because the preparation of the invention can directly reach the motoneurons in the spinal cord.

The dosage form includes various pharmaceutical preparations suited to the route of administration (such as liquid). For example, in the case of an injection preparation containing the gene as the active ingredient, the injection can be prepared by a conventional method, and, for example, it is dissolved in a proper solvent (buffer solution such as PBS, physiological saline, sterilized water, etc.), filtered and sterilized by a filter as required, and poured into an aseptic container. A carrier or other known matter may be added to the injection as required. In the case of liposome such as HVJ-liposome, liposome preparations can be manufactured in the dosage form of suspension, frozen matter, or frozen matter concentrated by centrifugal separation.

The content of the DNA in the preparation may be properly adjusted properly depending on the disease to be treated, age, body weight and other conditions of patients, and usually the dose of DNA of the invention is 0.0001 to 100 mg, preferably 0.001 to 10 mg, which is preferred to be administered once in every several days to every several months.

Same as in the case of HGF protein mentioned above, the invention also presents a remedy for ALS to be administered at a dose so that the expression level of HGF in the spinal cord may be more than 2 times before administration of HGF gene.

EXAMPLES

The invention is more specifically described below while presenting Examples, but it must be noted that the invention is not limited to these Examples alone.

Material and Method (1) Transgenic Mice

Transgenic G93A mice ((SOD1-G93A)1Gurd1) were purchased from Jackson Laboratory (Science, 264, 1772-1775, 1994). For the maintenance, male G93A mice were mated with female C57B6 mice, and genotyped by PCR and dot-blot hybridization.

Full-length rat HGF cDNA (Proc. Natl. Acad. Sci. U.S.A. 87, 3200-3204, 1990) tagged with KT3 epitope was amplified by PCR and inserted into the downstream of neuron-specific enolase promoter (Neuron, 18, 231-241, 1997) in pNSE-Ex vector (kindly provided by Dr. Doherty). For the subcloning, Not I site was generated in the pNSE-Ex vector by addition of linker. Full-base sequence of plasmid was confirmed. HGF-KT3 showed similar potency to human recombinant HGF in scattering assay of MDCK cell and in vitro survival assays of primary hippocampal neuronal culture. Transgenic mice were generated and analyzed for transgene integration as previously described (J. Cell. Biol., 128, 185-199, 1995; Proc. Natl. Acad. Sci. U.S.A., 95, 5269-5274, 1998) with slight modification. Briefly, transgenic cassette was excised from the vector by Sal I digestion and the DNA was injected into the embryo of C57B6 strain that has matched genetic background with G93A transgenic mice. Integration of transgene was examined by PCR and dot-blot using SV40 poly(A) sequence in the transgene construct. Expression of exogenous HGF was accessed by RNase protection assay, using probes covering 3' end of HGF-KT3 cDNA and 5' region of SV40 poly(A) signal sequence.

Progeny of NSE-HGF transgenic mice were crossed with G93A transgenic mice. The pups from one dam were housed in the same cage until onset of the phenotypes. After the first sign of onset, animals were separately kept. Food and water were supplied in the bottom for free access. When animal could not stand its body within 30 seconds, the time was used as the time of death.

(2) Quantification of HGF and c-Met RNA in the Ventral Horn

Quantitative competitive RT-PCR for the ventral horn of spinal cord was performed as previously reported (Brain Res. Brain Res. Protoc., 5, 190-197, 2000).

(3) RNase Protection Assay

RNase protection assay was preformed with an RPA II ribonuclease protection assay kit (Ambion, Austin, Tex.) as described previously (J. Cell. Biol., 123, 455-465, 1993; Science, 268, 1495-1499, 1995). To prepare an anti-sense cRNA probe specific for HGF mRNA, a 326-bp fragment encompassing 3' end part of poly(A) sequence of HGF-KT-3-polyA was inserted into pGEM-T vector. The plasmid was linearized and transcribed in the presence of a.-[$^{32}$P]CTP and prepared cRNA probe was used for the hybridization. Exogenous HGF RNA gives 326 bp protected band and endogenous HGF RNA gives shorter protected band (251 bp) because of the lacking of KT-3 and poly(A) sequence.

(4) Behavioral Tests

Behavioral tests were executed with 15 animals of each genotype from 6 families. Extension of hind limb is normally observed when a mouse is suspended in the air by its tail. Mice with motor neuron disease commonly show the retraction of hind limb. The score corresponds to the number of extending hind limbs. For a rotor rod test, mice were placed on the rod rotating at a speed of 20 rpm. The duration of each mouse remaining on the rod was measured. If animal could remain on the rod for 4 minutes, the test was finished and scored as 4 minutes. Footprint was collected by letting the mouse walk on a straight way after dipping its hind paw in the black ink. Stride was measured within the area showing regular walking.

(5) Histological Analyses

For the counting of the number of motoneurons, spinal cord was fixed by series of ethanol and serially section (14 μm) from L5 to L4 after embedding into the paraffin. Number of motoneurons (within L4-L5) on the ventral horn was counted from 20 sections on every seventh section. The number was counted on densely stained neurons by crystal violet with clear nucleolus in the defined area of ventral horn.

Antibodies specific for the c-Met (Santa Cruz, 1:100), antibodies specific for the HGF (Tokushu Meneki, 1:1000), antibodies specific for the human SOD (Sigma, 1:200), antibodies specific for the GFAP (Sigma, 1:1000), and antibodies specific for the caspase-1 (Santa Cruz, 1:500) were applied to the sections for 1 hour to 4 hours at room temperature or overnight at 4° C. after blocking with 5% goat serum and mouse IgG blocking reagent for 1 hour (M.O.M. kit, Vector Science). After washing, biotinylated or fluorescence labeled secondary antibody was applied and incubated for 15 minutes. For the fluorescence immunostaining, sections were then observed under the fluorescence microscope after counting staining with Hoechst 33342. Fluorescence image was captured and digitized by CCD camera (Hamamatsu), and the fluorescence level was measured using Adobe PhotoShop. To visualize the signal recognized by biotinylated secondary antibody, ABC solution was applied for 10 minutes and developed in the DAB solution. The specificity of each staining was tested as previously reported (Sun et al., 1999).

L5 root was dissected and fixed with 4% paraformaldehyde/0.25% glutaldehyde for overnight, and after postfix with osmium tetraoxide for 2 hours on ice, roots were dehydrated and embedded in Epon812. Embedded roots were sectioned (1 μm) and stained with toluidine blue. Morphology of samples was examined under the light microscope.

(6) Cell Culture

Primary astrocytes were cultured as described previously (Brain Res. Mol. Brain Res., 41, 259-268, 1996) with slight modification. Cerebral cortex of postnatal day 2 G93A mice or wildtype littermates was dissected and made into small pieces. Tissue blocks were dissociated by incubation with 0.25% trypsin and 100 μg/ml DNase I for 12 minutes in 37° C. water bath with shaking. The tissues were incubated by aspirating with pipette, and dissociated cells were plated in DF (high glucose DMEM/HamF12, 50:50) medium (GibCO BRL) with 10% fetal calf serum onto the poly-L-ornithin-coated dishes at indicated densities. Seven days after the plating when cells became confluent, cells were washed two times with PBS, and treated with indicated dose of recombinant HGF. Purity of the astrocytes was usually more than 95% after 7 days of culture, as examined by morphology or NSE/GFAP double staining.

(7) Western Blotting

Lumbar spinal cord lysate was prepared by RIPA buffer. Fifty micrograms of lysates was electrophoresed on a 10% SDS-polyacrylamide gel (SDS-PAGE) and transferred to PVDF membrane. The membrane was incubated with 5% non-fat skim milk in PBS overnight at 4° C. and anti-EAAT2 antibody (1:2,000, Chemicon) was applied for 2 hours. After washing, the membrane was incubated with HRP-conjugated anti-guinea pig IgG (1:3,000, Chemicon), and an ECL chemiluminescence reaction was performed (Amersham, Buckinghamshire, UK). The membrane was stripped and re-probed with anti-GFAP (1:3,000 Sigma), human SOD (1:500, Sigma), and anti-c-Met (1:400, Santa Cruz) antibody. Fifty micrograms of lysates was electrophoresed on a 12% SDS-PAGE and applied for phospho-Akt (Cell Signaling Tech.), Akt (Cell Signaling Tech.), Bcl-xL/s (Santa Cruz), and Bcl-2 (Santa Cruz) antibodies as described above. Band intensities were measured by Fluorochem image analyzer (IS-8000).

(8) Determination of HGF Concentration

HGF in tissues or plasma was measured by means of enzyme-linked immunosorbent assay (ELISA) using anti-rat HGF polyclonal antibody (Tokushu Meneki, Tokyo, Japan). The rat HGF ELISA system specifically detects rat and mouse HGF with similar affinity.

(9) Statistical Analysis

Statistical comparisons were determined by Student's t-test. For survival tests, statistical significance ($p<0.05$) was evaluated by log rank test.

Example 1

Expression and Regulation of HGF and c-Met in G93A Transgenic Mice

In motoneurons of G93A transgenic mice, it was studied by immunohistological analysis to observe presence or absence of c-Met/HGF receptor-like immunoreactivity (c-Met-IR). As a result, same as in motoneurons of wildtype littermates, localization of c-Met-IR was discovered in motoneurons of 2-month-old G93A mice (FIG. 1). At 8 months when G93A mice were at endstage, c-Met-IR was observed in many cells in the ventral horn, and the wildtype littermates of same age indicated a same level of c-Met-IR as those of 2 months of age (FIG. 1).

Figure 2:
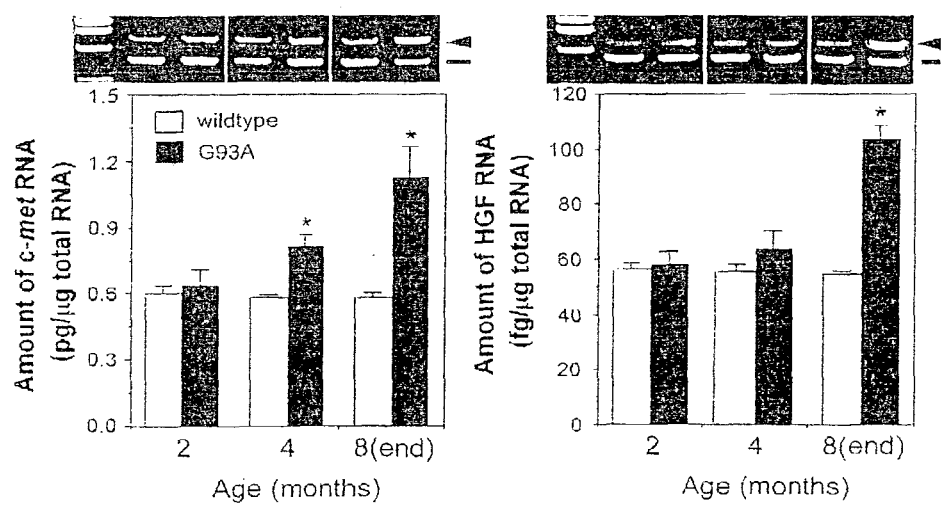
FIG. 2 is a graph showing results of quantification of HGF and c-met RNA in spinal cord by competitive RT-PCR, in progress stages of disease of G98A mice, in comparison with wildtype mice of same age. The axis of abscissas denotes the age, and the axis of ordinates represents the c-met RNA level (left) or HGF RNA level (right). In the figure, the arrowhead indicates the band of c-met or HGF, and the bar shows the band of competitor.

Quantification of HGF and c-met mRNA in the ventral horn of spinal cord in the progressive stage of G93A transgenic mice was determined by the competitive RT-PCR, and compared with that of wildtype mice of the same age. As a result, the expression level of c-met and HGF mRNA in the ventral horn of the spinal cord in which motoneurons localize is known to increase progressively in the process of ALS in G93A transgenic mice (FIG. 2). These results suggested the role of HGF in ALS motoneurons. Specifically, c-Met-IR was expressed not only in the remaining motoneurons, but also in the peripheral astrocytes, and the role of HGF in other cells than motoneurons was suggested. It was hence taught that HGF may be one of the endogenous factors for retarding the progress of the disease.

Example 2

Figure 3:
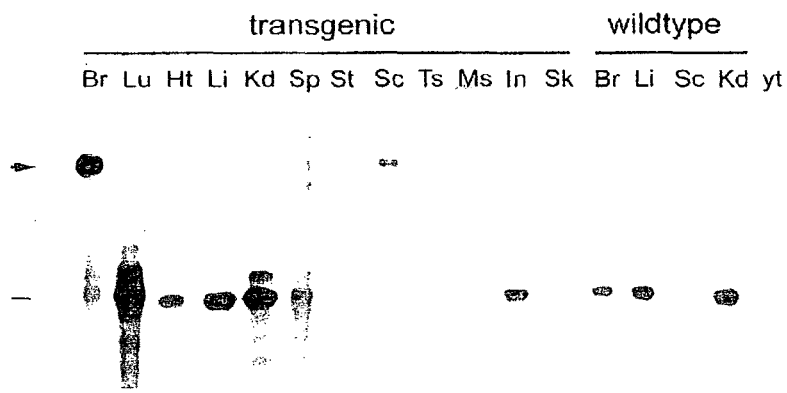
FIG. 3 is an electrophoretic photograph showing results of expression of exogenous HGF in each tissue of HGF transgenic mice prepared by using neuron-specific enolase promoter, analyzed by RNase protection assay. In the figure, the arrow indicates the band corresponding to the exogenous HGF, and the bar shows the band corresponding to the endogenous HGF. Also in the figure, Br is the brain, Lu is the lung, Ht is the heart, Li is the liver, Kd is the kidney, Sp is the spleen, St is the stomach, Sc is the spinal cord, Ts is the testis, Ms is the muscle, In is the intestine, and Sk is the skin.
Figure 4:
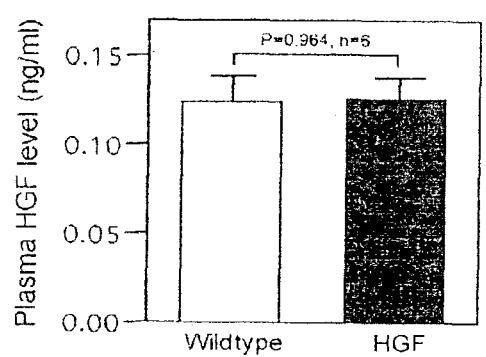
FIG. 4 is a graph showing the level of plasma HGF in 2-month-old wildtype and HGF transgenic mouse littermates (n=6). It was measured by means of enzyme-linked immunosorbent assay (ELISA).
Figure 5:
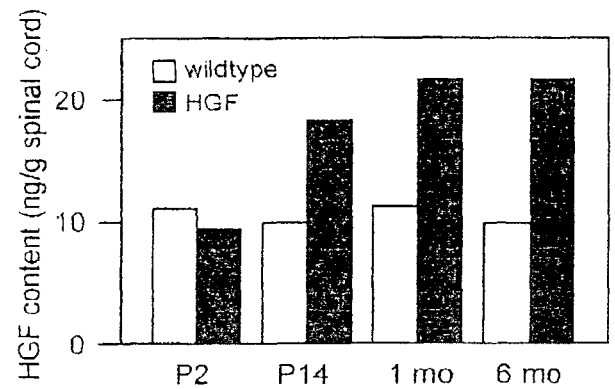
FIG. 5 is a graph showing ELISA analysis results of HGF contents in the whole spinal cord in wildtype and HGF transgenic mouse littermates at various growth stages after birth. In the figure, P2 is 2 days after birth, P14 is 14 days, 1 mo is 1 month of age, and 6 mo is 6 months of age.

Preparation and Characterization of Transgenic Mice Excessively Expressing HGF Neuron-specifically To study the effect of HGF in ALS, transgenic mice expressing rat HGF neuron-specifically were prepared by using neuron-specific enolase promoter (NSE). From eight independent lines of HGF transgenic mice, one line expressing the exogenous HGF specifically at relatively low level specifically in the nervous system was selected. FIG. 3, FIG. 4 and FIG. 5 show the characteristics of the HGF transgenic mouse lines. By RNase protection assay, exogenous HGF was known to be expressed in the brain and spinal cord specifically among 12 tissues being tested (arrow in FIG. 3). Among tissues of HGF transgenic mice, the endogenous and whole HGF levels in the plasma were not different from the levels in the wildtype littermates (FIG. 3 and FIG. 4). On the other hand, the level of HGF protein increased along with the growth of mice in the spinal cord, only after termination of principal differentiation of the spinal cord nerves after birth (FIG. 5).

Apparently, HGF transgenic mice could not be distinguished from the wildtype transgenic mice unless the genotype was determined. That is, no difference was noted in the size, body weight, morphology, behavior and changes in motor neuron system including many motoneurons and astrocytes, and weight of muscle at any stage of growth ever investigated. This fact proves the successful introduction of HGF specifically to the nervous system without effects on the growth (see FIG. 6 to FIG. 10, FIG. 19 and FIG. 20).

Example 3

Investigation of Effect of HGF on ALS (1)

To study the role of HGF on ALS, heterozygotes (+/−) of HGF transgenic mice were mated with heterozygotes (+/−) of G93A mice, and transgenic mice having HGF introduced directly into ALS neurons were prepared. By this mating, four different groups of mice were created, that is, wildtype (W), transgenic to HGF only (HGF), transgenic to G93A only (G93A), and double transgenic to both G93A and HGF (G93A/HGF).

Figure 6:
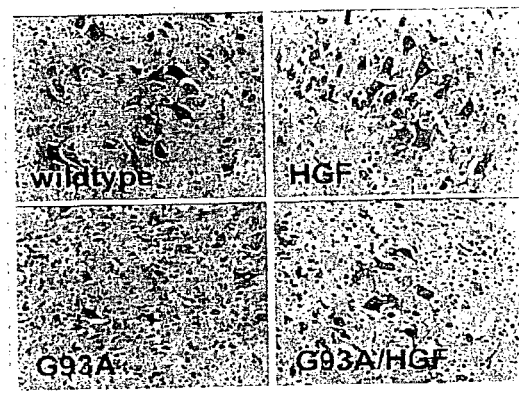
FIG. 6 is a microphotograph showing histological analysis results of number and morphology of motoneurons of ventral horn of lumbar spinal cord. In the figure, wildtype is wildtype mice, HGF is HGF single transgenic mice, G93A is G93A transgenic mice (ALS endstage), and G93A/HGF is double transgenic mice (ALS endstage).
Figure 7:
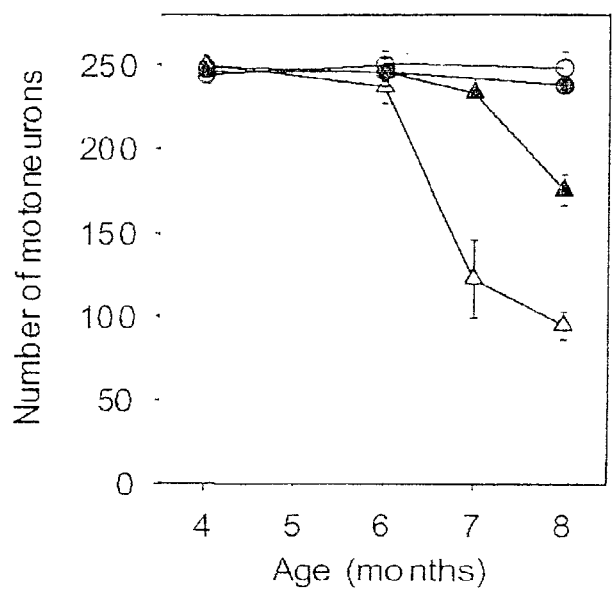
FIG. 7 is a graph showing quantitative comparison of number of motoneurons in the lumbar spinal cord in transgenic mice. In the figure, ○ is wildtype, ● is HGF single transgenic mice, Δ is G93A transgenic mice, and ▲ is double transgenic mice.

First of all, it was histologically analyzed to see if expression of HGF would trigger neuroprotective action on motoneurons. Results are shown in FIG. 6 and FIG. 7. Paraffin segments (14 m) of the ventral horn of lumbar spinal cord at endstage stained by crystal violet were evidently decreased in the number of motoneurons of G93A mice (G93A), and the remaining motoneurons were atrophied (FIG. 6). On the other hand, double transgenic littermates (G93A/HGF) maintained spinal cord motoneurons having many healthy forms evidently as compared with G93A mice (FIG. 6). Wildtype and HGF single transgenic mice presented a same number of healthy motoneurons (FIG. 6).

Using six independent animals in each group of mice, the number of motoneurons in lumbar spinal cord was quantitatively compared. As a result, at the age of 6 months, G93A mice began to lose motoneurons in the lumbar spinal cord gradually, and at the age of 8 months, only 40% of motoneurons were left over in G93A mice, as compared with motoneurons of wildtype or HGF single transgenic littermates (FIG. 7). By contrast, double transgenic littermates were evidently improved in the number of motoneurons as compared with G93A transgenic mice (FIG. 7).

The survival promoting activity of HGF on motoneurons has been proved to be different between the lumbar level and cervical level in chicken embryo, and it was tested to see if introduction of HGF would decrease death of motoneurons on the cervical level. As a result, in G93A mice, 55% of cervical motoneurons remained at the age of 8 months. It is a feature of the mice in this model that the death of motoneurons at the cervical level is smaller than at the lumbar level. In the double transgenic mice, at the cervical level, evidently, a greater number of motoneurons remained (87.8±2.4%), which suggests that HGF is effective on both lumbar and cervical motoneurons.

Using at least three independent animals in each group of mice, the effect of HGF on axon degeneration was studied by histological analysis.

Figure 8:
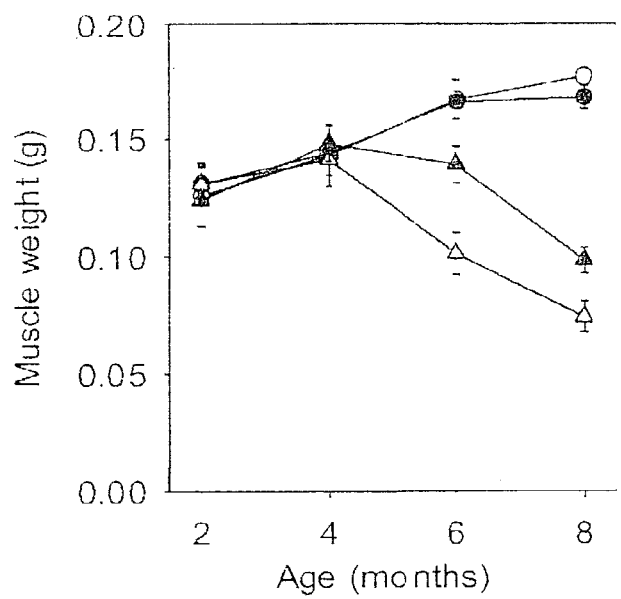
FIG. 8 is a graph showing the wet weight of gastrocnemius muscle of transgenic mice. In the figure, ○ is wildtype, ● is HGF single transgenic mice, Δ is G93A transgenic mice, and ▲ is double transgenic mice.
Figure 9:
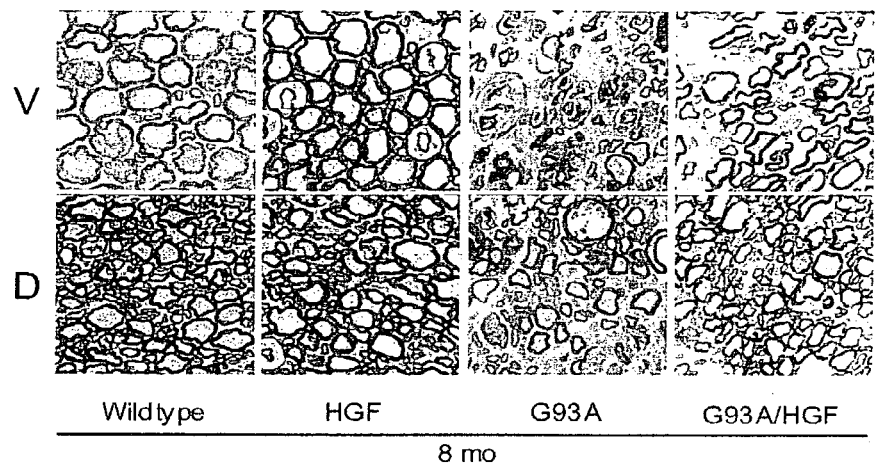
FIG. 9 is a microphotograph of segment (1 μm) of ventral root (V, upper panel) and dorsal root (D, lower panel) of 8-month-old transgenic mice.

Degeneration of axon of large-diameter the ventral root was observed in G93A mice at the age of 8 months (FIG. 9), while the axon degeneration of the ventral root was moderate in double transgenic littermates, and the ventral root was hardly changed. In the dorsal root, a medium degeneration was noted in G93A mice, but it was visually normal in double transgenic littermates (FIG. 9). These facts suggest that HGF effectively prevents degeneration of both ventral root and dorsal root. Further, in endstage double transgenic mice, if the ventral root was poor, the dorsal root was healthy. Therefore, HGF was known to have a neuroprotective effect not only on motoneurons but also on DRG sensory nerves relating to the ALS related neurotoxicity. Moreover, the neuroprotective effect of HGF was also suggested from the retarding effect of decrease in the gastrocnemius muscle (FIG. 8).

Example 4

Investigation of Effect of HGF on ALS (2)

Using the same four types of mice, it was tested to see if introduction of HGF would improve the start of paralysis, life span, and motility of ALS.

Figure 11:
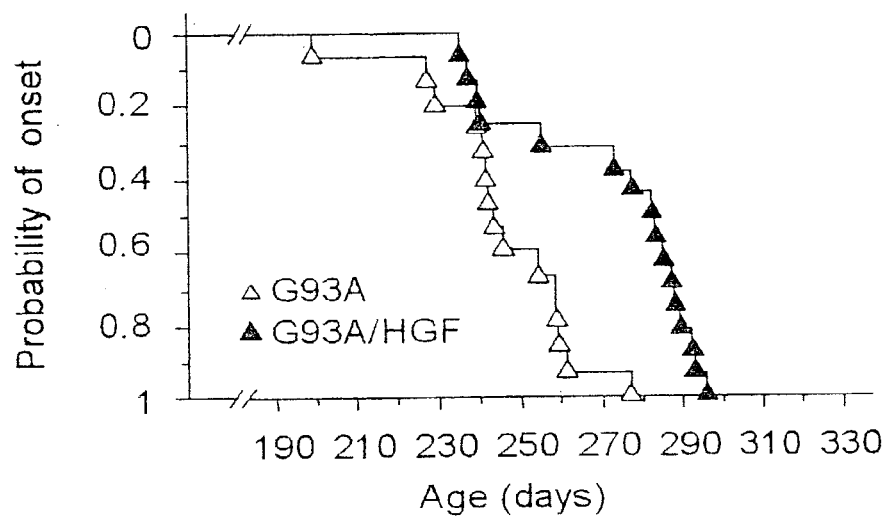
FIG. 11 is a graph showing comparative results of paralysis start in G93A transgenic mice (Δ, n=15) and G93A/HGF double transgenic mice (▲, n=16).

Start of paralysis was observed at the average age of 243.8±4.7 days (average±standard deviation, median=242±14 days) in heterozygote (+/−) G93A mice, and the start was evidently later in double transgenic mice (G93A/HGF), beginning at the age of 271.9±5.6 days (median 282.5±9.5 days, p=0.004) (FIG. 11).

Figure 12:
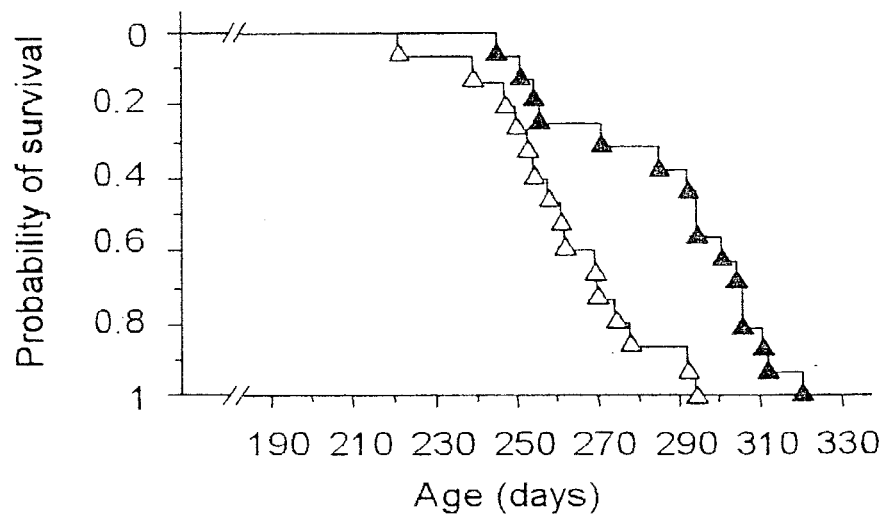
FIG. 12 is a graph showing comparative results of death start in G93A transgenic mice (Δ, n=15) and G93A/HGF double transgenic mice (▲, n=16).

Start of death in G93A mice was the average number of survival of 259.5±5.0 days (median=259±11 days). In double transgenic mice, the life was extended to 286.8±6.5 days, and the average life was extended by 27.3 days (median=294±14.5 days, p=0.003, FIG. 12).

Figure 13:
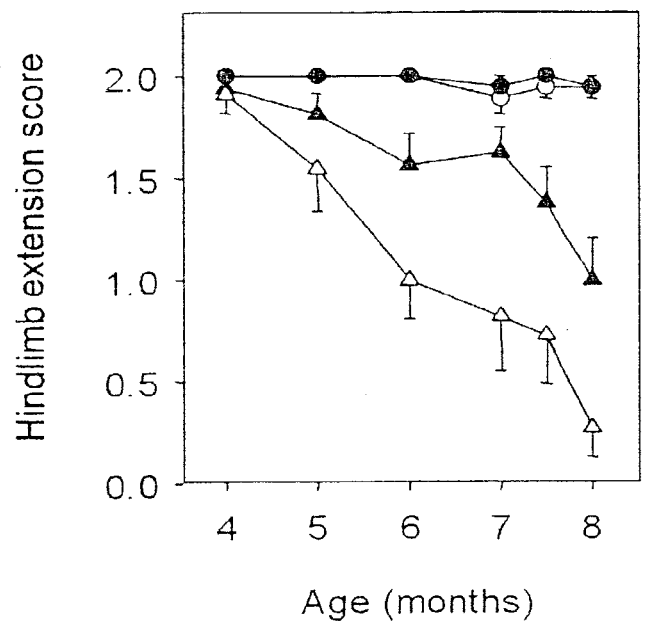
FIG. 13 is a graph showing results of measurement of hind limb stretch reflex in wildtype (○, n=14), HGF single transgenic mice (●, n=15), G93A transgenic mice (Δ, n=15), and double transgenic mice (▲, n=16).
Figure 14:
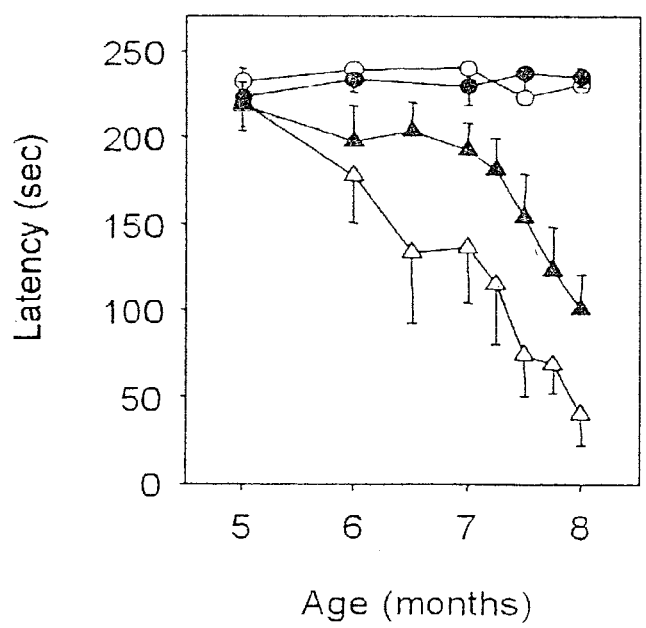
FIG. 14 is a graph showing results of measurement of holding time on rotor rod in wildtype (○, n=14), HGF single transgenic mice (●, n=15), G93A transgenic mice (Δ, n=15), and double transgenic mice (▲, n=16).
Figure 15:
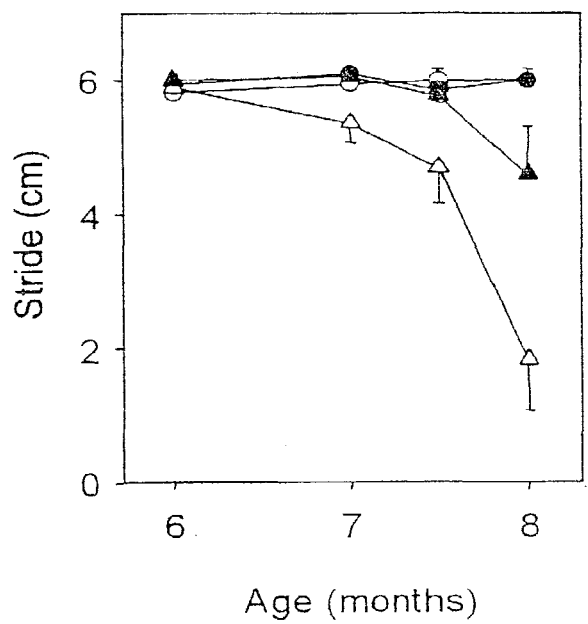
FIG. 15 is a graph showing results of measurement of stride in wildtype (○, n=14), HGF single transgenic mice (●, n=15), G93A transgenic mice (Δ, n=15), and double transgenic mice (▲, n=16).

Motility was tested by reflex of hind limb extension, holding time of rotor rod, and stride measurement. HGF single transgenic mice were similar in motility to wildtype littermates. G93A mice were decreased in hind limb extension from the age of 5 months, rotor rod capacity from 6 months, and stride progress from 7 months. On the other hand, double transgenic mice decrease very slowly in all functional parameters as compared with G93A mice (FIG. 13 to FIG. 15).

Figure 10:
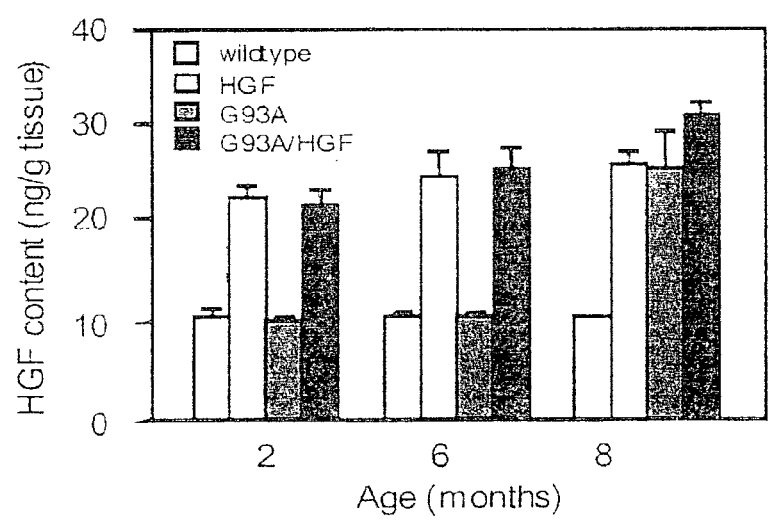
FIG. 10 is a graph showing ELISA analysis results of HGF level in the spinal cord at the age of 2, 6 and 8 months in transgenic mice.

FIG. 10 shows HGF protein levels of spinal cord in four groups in the progressive stages of ALS. HGF level was about 2 times higher at 2 months and 6 months in HGF transgenic mice and G93A/HGF littermates, which suggests that a small addition of HGF sufficiently improves the motor functions in 6 months, and extends the life span for 1 month. However, insufficient production of HGF in G93A/HGF double transgenic mice at 8 months, that is, same levels of HGF in HGF, G93A, and G93A/HGF at the endstage suggested possibility of reflection of imperfect improvement of ALS, and expression of HGF a higher level is expected.

Thus, expression of HGF gene on ALS neurons suggested an evident improvement of life span and motor function in ALS.

Example 5

Investigation of Action Mechanism of HGF on ALS (1)

In order to study the mechanism of possibility of decrease of motoneuron deaths in double transgenic mice, decrease of motor and sensory axon degeneration, and slow decrease of motor function, that is, to see if the transduced HGF would change the initial event of ALS, change the endstage event, or improve the speed of progress of disease without having effect on any specific event, one of the earliest signs of the disease was tested. Aggregation of mutant SOD1 is reported as an earliest event in animal models, and aggregation of SOD1 is reported in patients with familial ALS.

Figure 17:
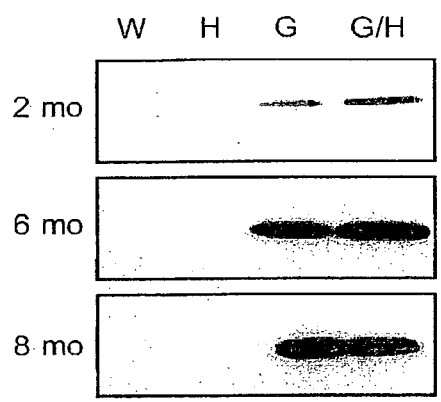
FIG. 17 is an electrophoretic photograph showing immunoblotting analysis results of amount of mutant SOD1 in the lumbar spinal cord of mice of wildtype (W), HGF single (H), G93A (G), and double transgenic (G/H). In the figure, 2 mo is 2 months of age, 6 mo is 6 months of age and 8 mo is 8 months of age.

The total volume of mutant SOD1 in spinal cord extract was investigated by immunoblotting by using an antibody specific to human SOD1 antibody, that is, capable of recognizing only the mutant human SOD1, not the endogenous mouse SOD1. Three independent animals were tested in each group. In both G93A and double transgenic mice, mutant SOD1 was detected from the age of 2 months. The total volume of mutant SOD1 increased in both G93A and double transgenic mice in a similar time course. The total volume of mutant SOD1 in G93A mice was not different from that of HGF littermates (FIG. 17).

Figure 16:
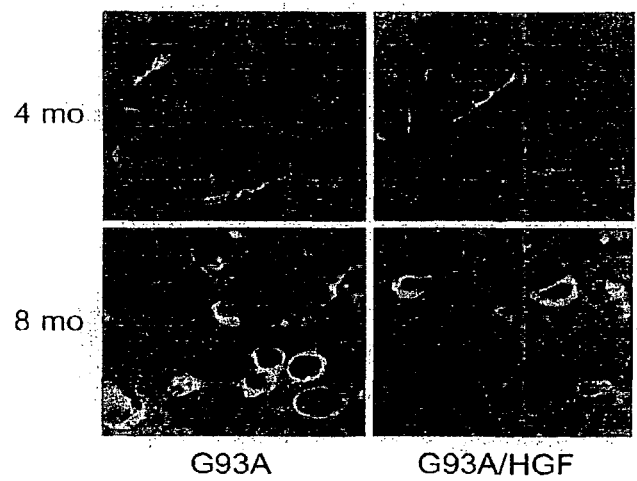
FIG. 16 is a microphotograph showing immunostaining analysis results of aggregation of mutant SOD1 in the lumbar spinal cord in G93A and G93A/HGF littermates in progressive stages of disease. In the figure, 4 mo is 4 months of age and 8 mo is 8 months of age.

Aggregation of SOD1 was investigated. Aggregation of mutant SOD1 in spinal cord was detected prominently at the ventral horn in initial stage (at the age of about 4 months) in G93A mice, and the volume of aggregation evidently increased at the age of 8 months in the endstage of animals (FIG. 16). Aggregation of mutant SOD1 in double transgenic mice corresponded to aggregation in G93A littermates at the age of 4 months (FIG. 16), and specific immunoresponse was not detected in wildtype or HGF single transgenic littermates. Aggregation of mutant SOD1 in double transgenic mice was evidently increased at 8 months (FIG. 16), and the volume seemed to be slightly less as compared with G93A littermates, but the difference was very small. These results suggested that HGF would not improve the origin of neurotoxicity and initial events of the disease in this model.

Caspase-1 is believed to play an important role in progress of ALS (Nature, 388, 31, 1997; J. Exp. Med., 185, 933-940, 1997). Therefore, to see if HGF would improve induction of caspase-1 or not, a double-labeled immunohistochemical method was attempted by using anti-caspase-1 antibody, and anti-tubulin III antibody staining mature neurons.

Caspase-1 immunoresponse (caspase-1-IR) was below the limit of detection in both wildtype and HGF littermates at any moment of test. In G93A mice, caspase-1-IR was specifically induced in large tubulin III immunostained cells at 6 months, and co-localized. It means induction of caspase-1 in motoneurons. Level of caspase-1 in G93A decreased at 8 months, and only a faint capase-1-IR was detected. In double transgenic mice, at 6 months of age, a very weak caspase-1-IR was indicated as compared with G93A mice in large tubulin III immunoresponse cells, which infers that HGF would decrease the level of induction of caspase-1 in motoneurons in the midstage of ALS.

Phosphorylation Akt is reported to be related to survival promotion activity of HGF in cerebral cortical neurons and renal epithelial cells, and HGF is known to induce Bcl-xL expression and block massive apoptosis in the liver in fluminant hepatitis models (Biochem. Biophys. Res. Commun., 244, 683-690, 1998; Hepatology, 30, 151-159, 1999). Accordingly, to explore the mechanism of HGF for decreasing apoptosis, phosphorylation of Akt and adjustment of Bcl-2 family gene were investigated.

Figure 18:
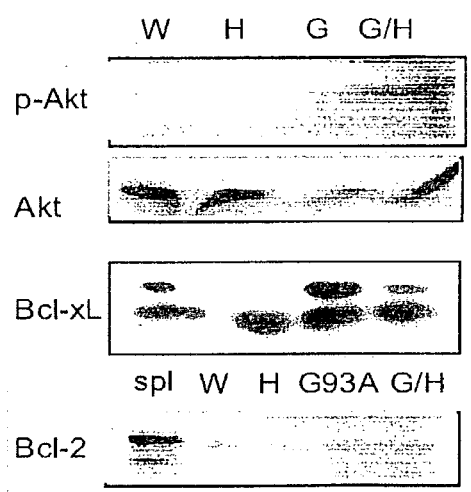
FIG. 18 is an electrophoretic photograph showing immunostaining results of phosphorylated Akt (p-Akt), Akt, Bcl-xL, and Bcl-2 in the lumbar spinal cord of 8-month-old mice of wildtype (W), HGF single (H), G93A (G), and double transgenic (G/H).
Figure 21:
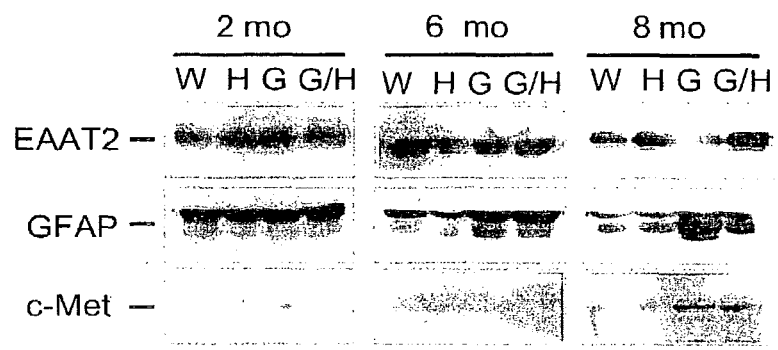
FIG. 21 is an electrophoretic photograph showing immunoblotting results of EAAT2, GFAP, and c-Met in the spinal cord of four types of mice at the age of 2, 6, and 8 months. In the figure, W is wildtype, H is HGF single transgenic, G is G93A transgenic, and G/H is double transgenic

By Western blotting, the amount of Akt was not changed in any littermate, and, by contrast, Akt was evidently phosphorylated specifically in the spinal cord of G93A/HGF mice at 8 months (FIG. 18). A considerably low level of Akt phosphorylation in the spinal cord of HGF mice seems to suggest the lower level of c-Met in HGF mice as compared with the level in double transgenic mice (FIG. 21). These results support the survival promotion activity of HGF partially through the activation of Akt.

Bcl-xL and Bcl-2 protein were not induced in the spinal cord at 8 months of age (FIG. 18).

As disclosed from these experiments, it was indicated that HGF retarded the progress of ALS by preventing caspase-1 induction in motoneurons and phosphorylation of Akt in the spinal cord.

Example 6

Investigation of Action Mechanism of HGF on ALS (2)

It has been indicated that glutamate-mediated excitotoxicity contributes to motoneuron degeneration of ALS by reduction of glutamate clearance.

Consistently with this hypothesis, it is reported that in the spinal cord and motor cortex of patients with sporadic ALS, glutamate transport activity is decreased remarkably (N. Engl. J. Med., 326, 1464-1468, 1992), and immunoreactivity for glial-specific glutamate transporter (EAAT2/GLT-1), which locates in astrocytes and is thought to be a major transporter to suppress glutamatergic neurotoxicity, selectively disappears (Ann. Neurol., 38, 73-84, 1995). The reduction of EAAT2 in G85R type ALS model transgenic mice (Neuron, 18, 327-338, 1997), and SOD1 mutants (A4V and I113T)-linked inactivation of a glial glutamate transporter in ALS (Nat. Neurosci., 2, 427-433, 1999) are also reported. The role of HGF on EAAT2 was studied because glutamatergic neurotoxicity was thought to play a part in motoneuron degeneration in ALS.

First, it was explored if c-Met-IR would be localized in reactive astrocytes or not, and if HGF would change the pathogenesis of astrocytes and level of glutamate transporter in reactive astrocytes. By double staining of spinal cord using anti-GFAP and anti-c-Met antibody, c-Met-IR was found to be localized in the remaining large neurons and GFAP positive reactive astrocytes. Not being contradictory to immunohistochemical results, levels of c-Met particularly increased at 8 months in G93A mice and double transgenic mice (FIG. 21, lower panel), which suggested that not only motoneurons but also astrocytes would be targets of HGF in ALS at 8 months (endstage).

Figure 19:
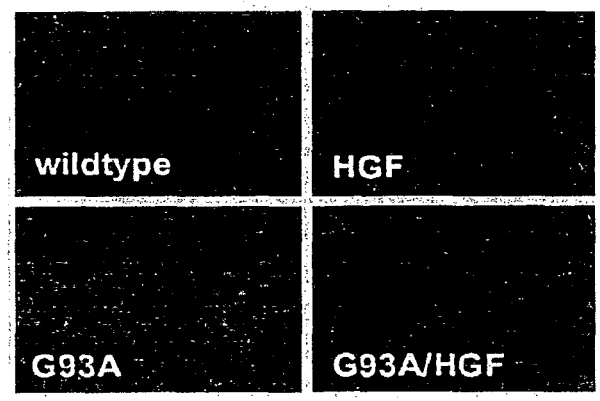
FIG. 19 is a microscopic photograph of GFAP immunohistological analysis results of ventral horn of lumbar spinal cord of 8-month-old mice of four types.
Figure 20:
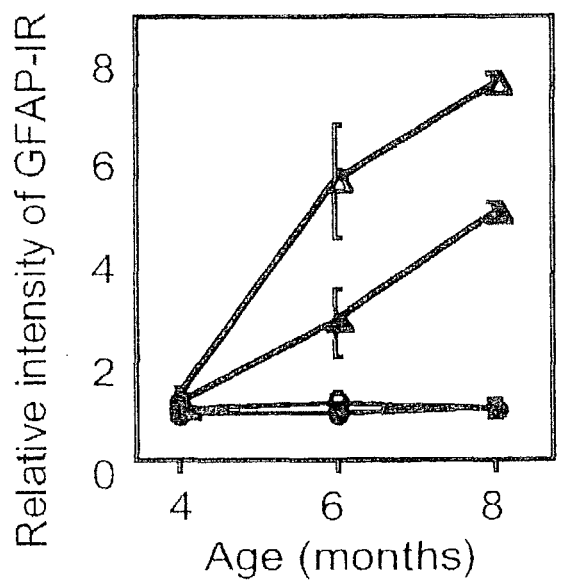
FIG. 20 is a quantitative graph immunohistological analysis by GFAP of FIG. 19. In the figure, ○ is wildtype, ● is HGF single transgenic, Δ is G93A transgenic, and ▲ is double transgenic (n=3 in each group).

In wildtype or HGF single transgenic mice, astrocytes were mainly white matter and localized near the central tubule, and very slightly localized in the ventral horn (FIG. 19). In G93A mice, reactive astrocytes progressively increased in the ventral horn at 6 months when motoneuron death was not observed in G93A mice (FIG. 19). By contrast, in double transgenic littermates, the number of reactive astrocytes in the ventral horn was extremely small (FIG. 19). Quantification of reactivity intensity of GFAP-IR disclosed small immunoresponse activities at the ventral horn of about 40% and 60%, as compared with those of G93A mice at 6 and 8 months, respectively (FIG. 20).

As a result of immunoblotting of EAAT2, GFAP and c-Met in spiral cord in mice at 2, 6 and 8 months of age, induction of GFAP was noted from the age of 6 months in both G93A mice and G93A/HGF mice, a specific EAAT2 down-regulation was observed in G93A mice at 8 months, and a specific up-regulation of c-Met was recorded in G93A and G93A/HGF mice at 8 months. In G93A/HGF mice, a total level of EAAT2 was maintained at 8 months.

Figure 22:
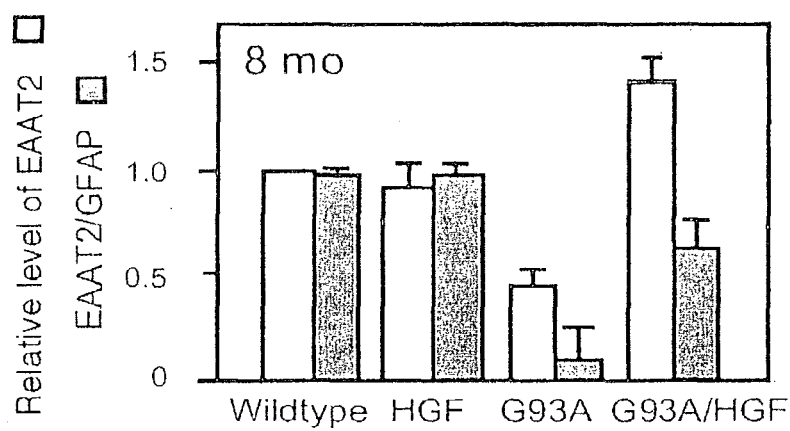
FIG. 22 is a graph showing the relative level of EAAT2 after standardization (EAAT2 level is divided by GFAP level in order to standardize) (in each group, n=4 mice).

The level of EAAT2 in G93A mice at 8 months of age was markedly decreased by 40%, as compared with that of wildtype or HGF single transgenic littermates (FIG. 22). By contrast, in double transgenic mice, as compared with wildtype or HGF single transgenic littermates, a higher level of EAAT2 (140%) was detected in the lumbar spinal cord (FIG. 22). To evaluate the level of EAAT2 in individual astrocytes, the level of EAAT2 was divided by the level of GFAP. Only 11% of EAAT2 were left over in G93A mice, while 63% of EAAT2 was left over in double transgenic mice (FIG. 22). Although increase of astrocytes began at 6 months, decrease of EAAT2 in astrocytes and induction of c-Met occurred parallel only at the endstage, which seems to be a noteworthy record.

Figure 23:
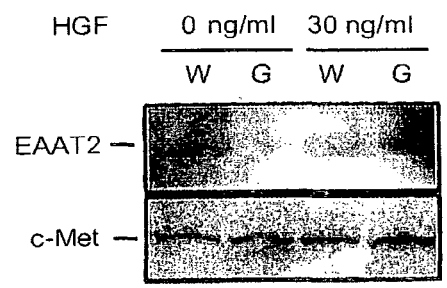
FIG. 23 is an electrophoretic photograph showing immunoblotting of EAAT2 and c-Met in astrocytes of primary culture after HGF treatment.
Figure 24:
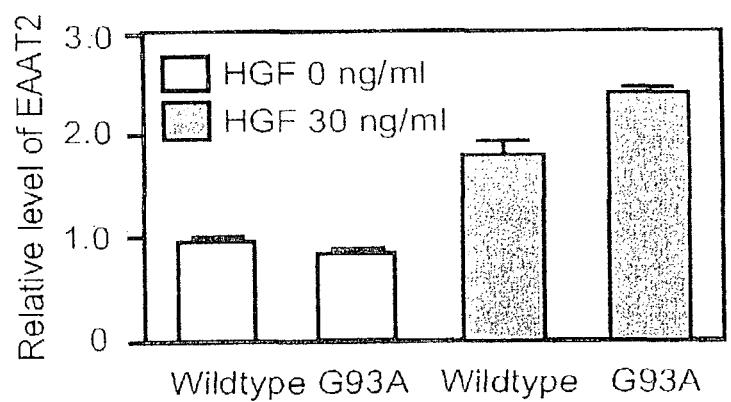
FIG. 24 is a quantitative graph showing results of immunoblotting of FIG. 23 (in each group, n=2).

As a result of investigation of action of HGF on primary culture of astrocytes, it was known that HGF treatment caused to increase the level of EAAT2 in primary culture of astrocytes in both G93A mice and wildtype littermates (FIG. 23 and FIG. 24). It means that prevention of decrease of EAAT2 in astrocytes directly owes to activity of HGF in astrocytes.

It was thus disclosed that double transgenic mice would maintain functional astrocytes at the endstage, while G93A mice would excessively produce nonfunctional astrocytes from the viewpoint of glutamate clearance.

Example 7

Progress Suppressing Effect of ALS by HGF Administration and HGF Gene Transduction In G93A mice as model of ALS, from the age of 6 months when a first sign of ALS is recognized, HGF protein preparation is administered to a proper site such as spinal cord at appropriate times and dose on consecutive days. In a control group, a preparation not containing HGF protein is administered. To evaluate the dose and number of administrations, the dose and the number of times are changed in groups. Further, in the HGF group and control group, progress suppressing effects of ALS are evaluated as mentioned in Examples 3 and 4. Possibility of usefulness of HGF as remedy for ALS will be confirmed when the ALS progress suppressing effect will be recognized in the HGF group.

By conducting a similar experiment by using HGF gene instead of HGF, usefulness of HGF gene as remedy for ALS will be confirmed.

Pharmaceutical Preparation 1

A solution containing 1 mg of HGF, 1 g of mannitol and 10 mg of polysorbate 80 in 100 ml of physiological saline was aseptically prepared, and dispensed in 1 ml vials, and was freeze-dried and sealed, and freeze-dry preparations were obtained.

Pharmaceutical Preparation 2

An aqueous solution containing 1 mg of HGF and 100 mg of human serum albumin in 100 ml of 0.02M phosphate buffer (containing 0.15 M NaCl and 0.01% polysorbate 80, pH 7.4) was aseptically prepared, and dispensed in 1 ml vials, and was freeze-dried and sealed, and freeze-dry preparations were obtained.

INDUSTRIAL APPLICABILITY

The invention presents a therapeutic agent (and progress suppressant) for ALS containing HGF and/or HGF gene as active ingredient. HGF has an effect of improving the motor function of ALS and life span through two actions, that is, direct neuronutrient factor activity on motoneurons, and indirect improving action of glutamate cytotoxicity on motoneurons by maintaining the level of glutamate transporter in astrocytes. Such bifunctional growth factor has not been known so far, and therefore HGF and/or HGF gene can be used as an effective therapeutic agent not known in the past.

The invention claimed is:

1. A method for treating amyotrophic lateral sclerosis (ALS), comprising:
   (i) administering Hepatocyte Growth Factor (HGF) to a patient suffering from ALS by intraspinal or intraventricular administration dose of HGF in the range from 0.001 to 1000 mg per day that is effective to raise the level of HGF in the spinal cord of the patient to at least 2-fold higher than the level of HGF in the spinal cord of the patient before treatment; and
   (ii) measuring the level of HGF in the spinal cord of the patient before and after the treatment, thereby confirming that the latter level is at least 2-fold higher than the former level.

2. The method as claimed claim 1, by which activity of caspase-1 in motoneurons of the patient suffering from ALS is suppressed.

3. The method as claimed claim 1, by which phosphorylation of protein kinase B (Akt) is increased in the patient suffering from ALS.

4. The method as claimed in claim 1, wherein ALS is familial amyotrophic lateral sclerosis (FALS) of which the patient carries mutations in the gene encoding $Cu^{2+}/Zn^{2+}$ superoxide dismutase (SOD1) .

5. The method of claim 1, in which the dose of HGF that is administered is in the range from 0.01 to 100 mg/day.

6. A method for delaying start of paralysis of a patient suffering from ALS, comprising:
   (i) administering Hepatocyte Growth Factor (HGF) by intraspinal or intraventricular administration to a patient suffering from ALS dose of HGF in the range from 0.001 to 1000 mg per day that is effective to raise the level of HGF in the spinal cord of the patient at least 2-fold;
   (ii) delaying start of paralysis of the patient; and
   (iii) measuring the level of HGF in the spinal cord of the patient before and after the HGF administration, thereby confirming that the latter level is at least 2-fold higher than the former level.

7. The method of claim 6, in which the dose of HGF that is administered is in the range from 0.01 to 100 mg/day.

8. A method for extending the life span of a patient suffering from ALS, comprising:
   (i) administering Hepatocyte Growth Factor (HGF) by intraspinal or intraventricular administration to a patient suffering from ALS dose of HGF in the range from 0.001 to 1000 mg per day that is effective to raise the level of HGF in the spinal cord of the patient at least 2-fold;
   (ii) extending the life span of the patient; and
   (iii) measuring the level of HGF in the spinal cord of the patient before and after the HGF administration, thereby confirming that the latter level is at least 2-fold higher than the former level.

9. The method of claim 8, in which the dose of HGF that is administered is in the range from 0.01 to 100 mg/day.

10. A method for retarding decrease in muscle of a patient suffering from ALS, comprising:
   (i) administering Hepatocyte Growth Factor (HGF) by intraspinal or intraventricular administration to a patient suffering from ALS dose of HGF in the range from 0.001 to 1000 mg per day that is effective to raise the level of HGF in the spinal cord of the patient at least 2-fold;
   (ii) retarding decrease in muscle of the patient; and
   (iii) measuring the level of HGF in the spinal cord of the patient before and after the HGF administration, thereby confirming that the latter level is at least 2-fold higher than the former level.

11. The method of claim 10, in which the dose of HGF that is administered is in the range from 0.01 to 100 mg/day.

* * * * *